US008512704B2

(12) United States Patent
Jahn-Hofmann et al.

(10) Patent No.: US 8,512,704 B2
(45) Date of Patent: Aug. 20, 2013

(54) TMEM27 ANTIBODY

(75) Inventors: Kerstin Jahn-Hofmann, Neu-Isenburg (DE); Sannah Zoffmann Jensen, Basel (CH); Hugues Matile, Basel (CH); Cristiano Migliorini, Geneva (CH); Haiyan Wang, Allschwil (CH)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/388,974

(22) PCT Filed: Jul. 30, 2010

(86) PCT No.: PCT/EP2010/061078
§ 371 (c)(1),
(2), (4) Date: Feb. 3, 2012

(87) PCT Pub. No.: WO2011/015521
PCT Pub. Date: Feb. 10, 2011

(65) Prior Publication Data
US 2012/0134927 A1  May 31, 2012

(30) Foreign Application Priority Data

Aug. 4, 2009  (EP) .................................... 09167160

(51) Int. Cl.
*A61K 39/395* (2006.01)
*C12N 5/12* (2006.01)
*C07K 16/28* (2006.01)

(52) U.S. Cl.
USPC ................... 424/144.1; 424/141.1; 424/1.49; 530/388.1; 530/388.22; 435/326

(58) Field of Classification Search
None
See application file for complete search history.

(56) References Cited

FOREIGN PATENT DOCUMENTS

WO   2006/133333   12/2006

OTHER PUBLICATIONS

Akpinar et al., "Tmem27: A cleaved and shed plasma membrane protein that stimulates pancreatic beta cell proliferation" Cell Metabolism 2(6):385-397 (Dec. 1, 2005).
Akpinar et al., "Collectrin, a transmembrane glycoprotein expressed in beta-cells, is a target of Hnf1 alpha and is developmentally regulated in the embryonic pancreas" 64th Annual Meeting of the American Diabetes Association; Orlando, FL 53( Suppl 2):A378 (Jun. 1, 2004).
Zhang et al., "Collectrin, a collecting duct-specific transmembrane glycoprotein, is a novel homolog of ACE2 and is developmentally regulated in embryonic kidneys" Journal of Biological Chemistry 276(20):17132-17139 (Jan. 31, 2001).
Malakauskas et al., "Increased insulin sensitivity in mice lacking collectrin, a downstream target of HNF-1alpha" Molecular Endocrinology 23(6):881-892 (Jun. 1, 2009).
ISR for PCT/EP2010/061078, (2010).
Akpinar et al., "Tmem27: A cleaved and shed plasma membrane protein that stimulates pancreatic beta cell proliferation" Cell Metabolism 2(6):285-297 (Dec. 1, 2005).

*Primary Examiner* — Prema Mertz
(74) *Attorney, Agent, or Firm* — Jennifer K. Holmes

(57) ABSTRACT

The present invention relates to an antibody directed to a beta cell marker protein, in particular to an antibody directed to the protein TMEM27.

10 Claims, 7 Drawing Sheets

Figure 1:
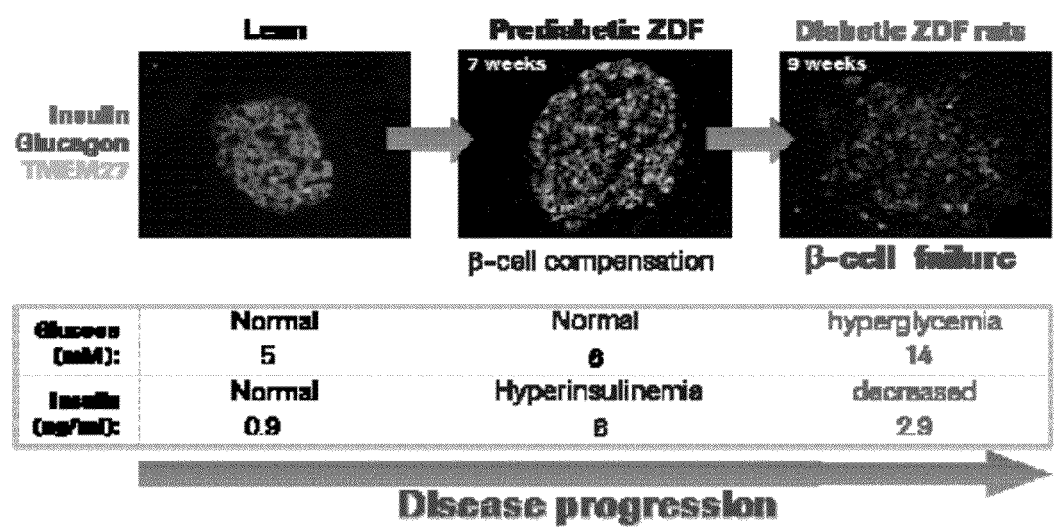

Fig. 4a
Fab 3.3µg/ml + IgG 1µg/ml
→ 488
Fab 66nM + IgG 6.6 nM
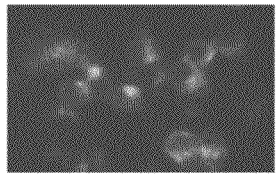
Fig. 4b
Fab 8/9-Alexa555 -
3.3µg/ml
66nM
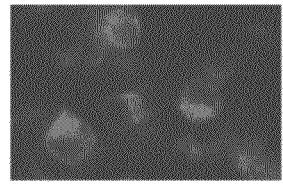
Fig. 4c
IgG 8/9-Alexa488 10µg/ml
66nM
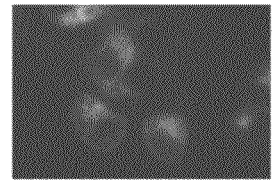
Fig. 4d
Fab 3.3µg/ml + IgG 1µg/ml →
555
Fab 66nM + IgG 6.6 nM
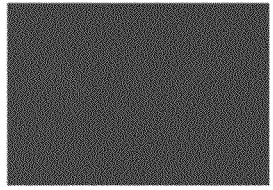
Fig. 4e
nt
Fig. 4f
IgG 8/9-Alexa488 3.3µg/ml
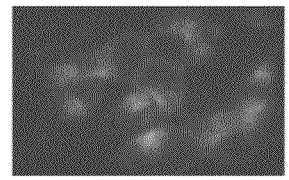
Fig. 4g
Fab 3.3µg/ml + IgG 1µg/ml →
488+555
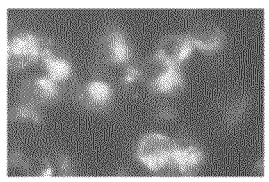
Fig. 4h
Fab 8/9-Alexa555 -
0.33µg/ml
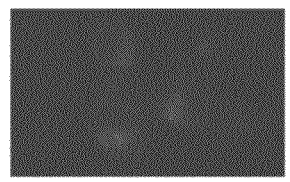
Fig. 4i
IgG 8/9-Alexa488 1.0 µg/ml
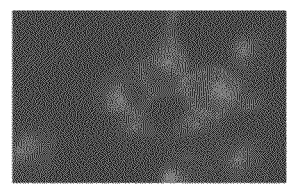
Fig. 4j
neg.
Fig. 4k
IgG 8/9-Alexa488 0.33µg/ml
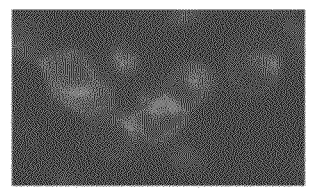

8A

8B

8C

8D

8E

8F

8G

8H

8 I

8J

8 K

8L

TMEM27 ANTIBODY

CROSS REFERENCE TO RELATED APPLICATIONS

This application is a National Phase filing under 35 U.S.C. §371 of International Application No. PCT/EP2010/061078 having an international filing date of Jul. 30, 2010, the entire contents of which are incorporated herein by reference, and which claims benefit under 35 U.S.C. §119 to European Patent Application No. 09167160.2 filed Aug. 4, 2009.

SEQUENCE LISTING

The instant application contains a Sequence Listing which has been submitted via EFS-Web and is hereby incorporated by reference in its entirety. Said ASCII copy, created on Feb. 3, 2012, is name P4842R1 Seq List.txt, and is 6,294 bytes in size.

The present invention relates to an antibody directed to a beta cell marker protein, in particular to an antibody directed to the protein TMEM27.

Loss of functional beta-cell mass underlies the pathogenesis of both type 1 and type 2 diabetes. Noninvasive imaging of beta-cell mass in vivo would therefore provide a valuable diagnostic and research tool for quantifying progression to diabetes and response to therapeutic intervention. In addition, non-invasive and targeted beta-cell siRNA delivery in vivo would be very valuable for both research and therapy.

The transmembrane protein Tmem27 (Collectrin) is expressed in pancreatic β-cells where it regulates pancreatic β-cell mass, and insulin secretion. Tmem27 is inactivated at the plasma membrane by proteolytic cleavage and shedding.

Therefore, there is a need for a diagnostic and/or research tool for quantifying beta-cell mass and there is a need for a tool for targeted drug delivery to beta-cells.

It is an object of the present invention to provide an antibody directed to an epitope of a Tmem27 polypeptide.

In a preferred embodiment the antibody is directed to human Tmem27 polypeptide.

In a further embodiment, the antibody is a monoclonal antibody, preferably a humanized antibody.

In a further embodiment, the antibody has been produced by immunizing suitable animals with whole cells expressing the Tmem27 polypeptide, preferably human Tmem27 polypeptide.

In a further preferred embodiment, the antibody comprises a CDR3 of a $V_H$ domain of an antibody obtainable from hybridoma cell line TMEM27-8/9 (DSM ACC2995) and a CDR3 of a $V_L$ domain of an antibody obtainable from hybridoma cell line TMEM27-8/9 (DSM ACC2995).

In a further preferred embodiment, the antibody comprises CDR1 to CDR3 of the $V_H$ domain of an antibody obtainable from hybridoma cell line TMEM27-8/9 (DSM ACC2995) and CDR1 to CDR3 of the $V_L$ domain of an antibody obtainable from hybridoma cell line TMEM27-8/9 (DSM ACC2995).

In a further preferred embodiment, the antibody is a chimeric antibody comprising a $V_H$ domain and a $V_L$ domain of an antibody obtainable from hybridoma cell line TMEM27-8/9 (DSM ACC2995).

In a further preferred embodiment, the antibody is produced by hybridoma cell line TMEM27-8/9 which was deposited with the DSMZ (German Collection of Microorganisms and Cell Cultures) on May 27, 2009 and received the deposit number DSM ACC2995.

In a second object, the present invention relates to the use of the antibody of the present invention for the manufacturing of a medicament for the treatment of a disease involving modulation of TMEM27 cleavage and its signaling pathway. The disease is preferably diabetes.

In a further embodiment, the antibody of the present invention is used as a tool for the intracellular delivery of active compounds. The active compound is preferably covalently coupled to the antibody. The "active compound" can be any suitable molecule, including DNA, RNA, siRNA, a protein, a peptide, or a pharmaceutically active agent, such as, for example, a toxin, an antibiotic, an antipathogenic agent, an antigen, an antibody, an antibody fragment, an immunomodulator, an enzyme, or a therapeutic agent. The antibody of the present invention is suitable for intracellular delivery of active compounds since the antibody allows a targeted intracelluar delivery of the active compounds by specifically targeting pancreatic beta-cells.

In a further embodiment, the antibody of the present invention can be used for in vivo imaging of beta cell islet and beta-cell mass in a pancreas of a animal, preferably a human being. A suitable method for in vivo imaging is e.g. Immuno-PET (Positron Emission Tomography). Immuno-PET is based on the coincidental detection of a mononclonal antibody labelled with a positron-emitting radionuclide. The following positron emitters can be used for immuno-PET: gallium-68 ($^{68}$Ga; $t_{1/2}$, 1.13 hours), fluorine-18 ($^{18}$F; $t_{1/2}$, 1.83 hours), copper-64 ($^{64}$Cu; $t_{1/2}$, 12.7 hours), yttrium-86 ($^{86}$Y; $t_{1/2}$, 14.7 hours), bromine-76 ($^{76}$Br; $t_{1/2}$, 16.2 hours), zirconium-89 ($^{89}$Zr; $t_{1/2}$, 78.4 hours), and iodine-124 ($^{124}$I; $t_{1/2}$, 100.3 hours) [The Oncologist, Vol. 12, No. 12, 1379-1389, December 2007)].

The distribution of a PET conjugate in a patient can be monitored by detection of the annihilation photon pairs with a PET camera. A PET camera consists of a ring of detectors placed around the body of the patient. If two photons are registered by detectors on opposite sides of the body within a very short time interval (typically 5-15 nanoseconds), it is assumed that somewhere along the line between the two detectors an annihilation event has taken place. By calculating the crossing of all lines, the location of the radiation source (radiolabelled mAb) can be determined.

The term "antibody" encompasses the various forms of antibody structures including but not being limited to whole antibodies and antibody fragments. The antibody according to the invention is preferably a humanized antibody, chimeric antibody, or further genetically engineered antibody as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a $V_H$ domain, namely being able to assemble together with a $V_L$ domain, or of a $V_L$ domain binding to ANG-2, namely being able to assemble together with a $V_H$ domain to a functional antigen binding site and thereby providing the property.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See e.g. Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "Tmem27 polypeptide" is used herein to refer to native Tmem27 polypeptide from any animal, e.g. mammalian, species, including humans, and Tmem27 variants. The Tmem27 polypeptides may be isolated from a variety of sources, including human tissue types or prepared by recombinant and/or synthetic methods. The amino acid sequence of human Tmem27 polypeptide is given in Seq. Id. No. 7.

In a further object, the present invention provides a conjugate comprising an antibody of the present invention and an active compound covalently linked to the antibody.

In a preferred embodiment, the active compound is a toxin or a siRNA molecule, preferably a siRNA molecule.

A method of preparing an siRNA-antibody conjugate in the form A-X-Y by covalently bonding the antibody of the present invention to an end group of an siRNA molecule, the method comprising: selecting a predetermined siRNA molecule; and covalently bonding the siRNA molecule to the antibody of the present invention, wherein A is the antibody of the present invention, X is a linker-mediated covalent bond, and Y is an siRNA molecule.

The method of preparing a siRNA-antibody conjugate can comprise activating a functional group of siRNA, and covalently bonding the activated functional group to the antibody. The functional group to be activated can include, but is not limited to, an amine group, thiol group, phosphate group, or combinations thereof. In some embodiments, the material which activates the functional group of siRNA comprises 1-ethyl-3,3-diethylaminopropyl carbodiimide, imidazole, N-hydroxylsuccinimide, dichlorohexyl-carbodiimide, N-maleimidopropionic acid, N-maleimidopropyl-oxylsuccinimide ester, N-succinimidylpyridyldithiopropionate, or combinations thereof. Further methods for preparing the siRNA antibody conjugate of the present invention can be found in the Handbook of Cell Penetrating Peptides, Chapter 18, Second Edition, April 2006, Editor: Ülo Langel.

In a further object, the present invention provides a pharmaceutical composition comprising an antibody or a conjugate of the present invention and a pharmaceutically acceptable carrier For better administration, the composition can further comprise at least one kind of pharmaceutically acceptable carrier in addition to the above-described active ingredients. Examples of such carriers include saline solution, sterile water, Ringer's solution, buffered saline solution, dextrose solution, maltodextrin (aqueous) solution, glycerol, ethanol and mixtures thereof. If needed, typical additives, such as, an antioxidant, a buffer, a bacteriostatic agent and the like, can be added. Moreover, the composition can be pharmaceutically produced for injection in the form of an aqueous solution, suspension, emulsion and so forth by adding more additives, such as, a diluting agent, a dispersing agent, a surfactant, a bonding agent and a lubricant.

The pharmaceutical composition of the invention can be brought into contact with the body through diverse administration routes, including intravenous administration, intramuscular administration, intra-arterial administration, intramedullary administration, intrathecal administration, intracardiac administration, percutaneous administration, hypodermic administration, intraperitoneal administration, sublingual administration, and topical administration.

For such clinical administration, the pharmaceutical composition of the present invention can be prepared in an adequate product using conventional techniques.

Antibodies may be produced using recombinant methods and compositions, e.g., as described in U.S. Pat. No. 4,816,567. In one embodiment, isolated nucleic acid encoding an anti-TMEM27 antibody described herein is provided. Such nucleic acid may encode an amino acid sequence comprising the $V_L$ and/or an amino acid sequence comprising the $V_H$ of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-TMEM27 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody of the present invention, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*). After expression, the antibody may be isolated from the bacterial cell paste in a soluble fraction and can be further purified.

Methods to clone antibody genes from hybridomas producing monoclonal antibodies are know to a person skilled in the art. For example, the genetic information for the variable heavy and light chain domains ($V_H$ and $V_L$) can be amplified from hybridoma cells using polymerase chain reaction (PCR) with immunoglobulin-specific primers (Methods Mol. Med. 2004; 94:447-58). The nucleic acid encoding the variable heavy and light chain domains ($V_H$ and $V_L$) can then be cloned in a suitable vector for expression in host cells.

SHORT DESCRIPTION OF THE FIGURES

Figure 2:
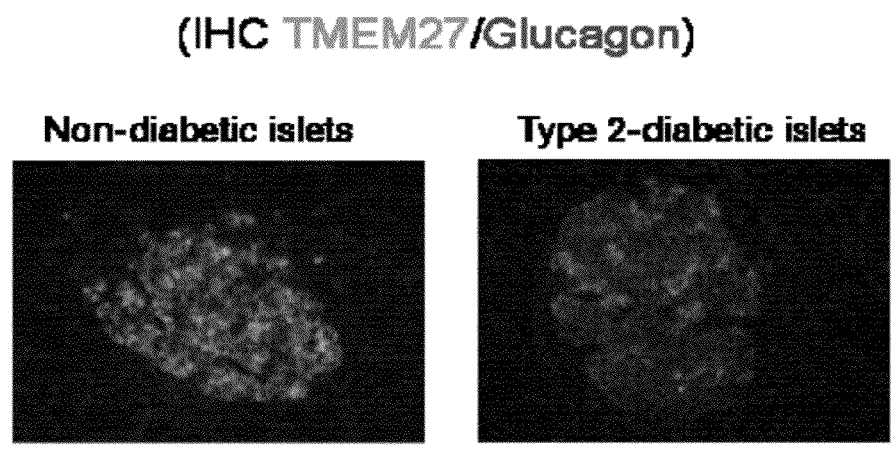
Figure 3:
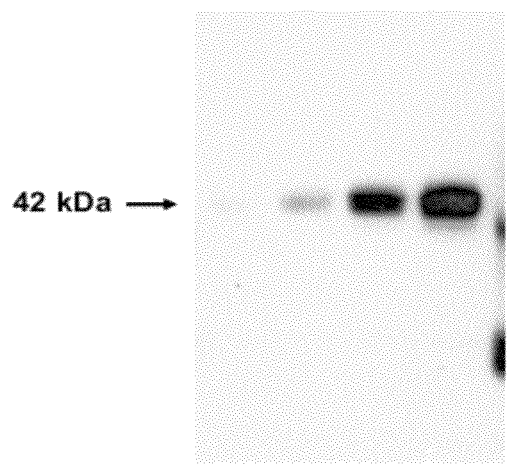
Figure 5:
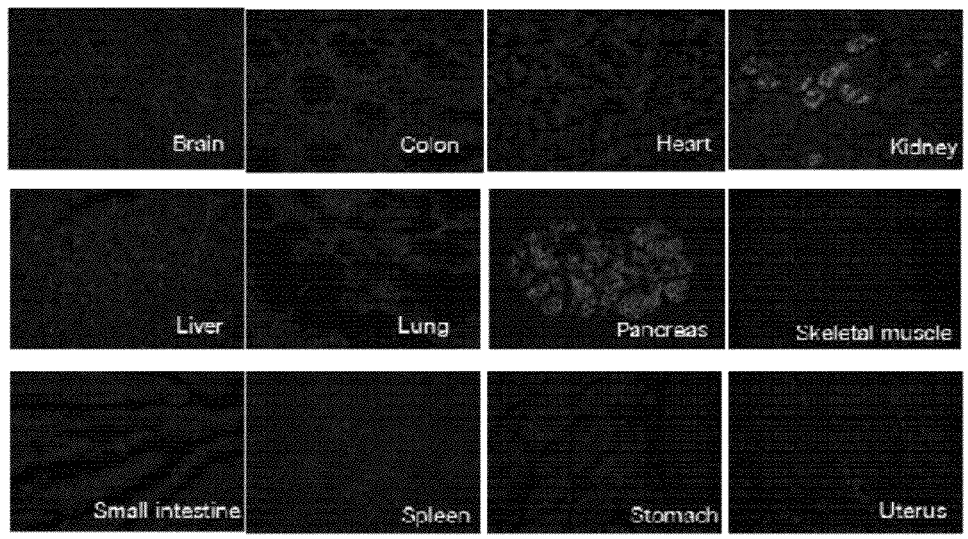
Figure 6A:
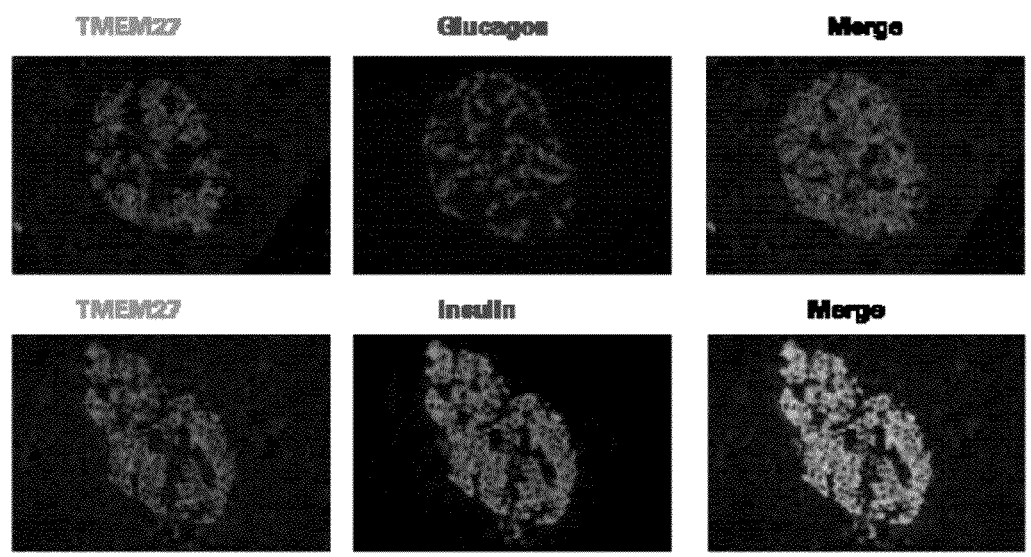
Figure 6B:
Figure 7:
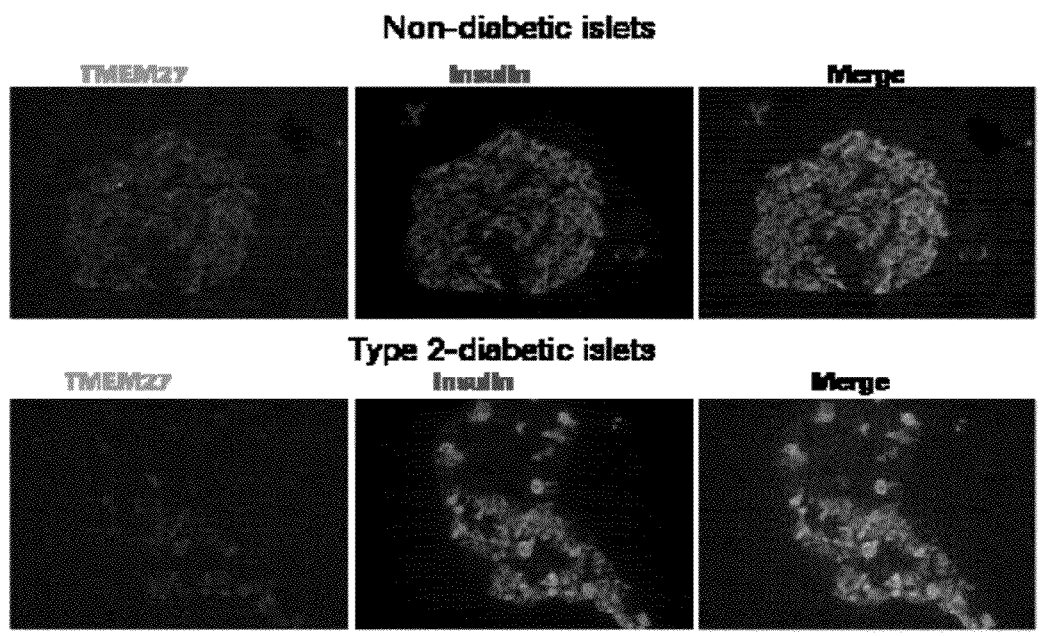

FIG. 1 shows that Beta-cell TMEM27 protein levels correlate with diabetes progression. Paraffin-sections of pancreas from lean or ZDF rats at 7- or 9-week age were stained with antibodies against insulin (red), glucagon (blue) and TMEM27 (green). There is an increased expression of TMEM27 in pancreatic sections of insulin-resistant but normal glycemic ZDF rats at 7-weeks, which correlate with expansion of beta-cell mass, FIG. 2 shows that TMEM27 protein levels are reduced in type 2 diabetic patients. Immunohistochemistry staining of paraffin sections of pancreas from normal glycemic donor and type 2 diabetic patients shows that TMEM27 (green), which does not colocalize with glucagon (red) is largely reduced in type 2 diabetic islets, FIG. 3 shows a Western blot of INS-1 stable cell lines allowing inducible expression of human TMEM27 in a doxycycline-dependent manner. hTMEM27 protein could be induced dose-dependently by doxycycline, FIG. 4a-4k show the results of incubation of TMEM27-8/9-Alexa488-IgG and TMEM27-8/9-Alexa555-Fab with living INS-hTMEM27 cells, FIG. 5 shows immunohistochemistry staining of FDA-approved human tissue microarrays. Paraffin sections of human tissue microarrays were stained with Alexa488-conjugated anti-TMEM27 (clone 8/9), FIGS. 6a and 6b show immunohistochemistry staining of human and monkey pancreas. Paraffin sections of human and monkey pancreas were stained with Alexa488 conjugated TMEM27 (8/9), FIG. 7 shows that TMEM27 protein levels are reduced in type 2 diabetic monkey. Immunohistochemistry staining of paraffin sections of pancreas from normal glycemic or type 2 diabetic monkeys shows that TMEM27 (green), which colocalizes with insulin (red) is largely reduced in type 2 diabetic monkey islets, FIG. 8*a*-8*j* show IgG mediated siRNA cellular uptake using an antibody recognizing TMEM27 (8*a*-8*i*) or mGluR7 receptor (8*j*-8*l*) and FIGS. 9*a* and 9*b* show the quantified fluorescence from surface immuno staining and the intracellularly accumulated siRNA marker Cy5.

EXPERIMENTAL PART

Generation of INS-1 Stable Cell Lines Allowing Inducible Expression of Human TMEM27 in a Doxycycline-Dependent Manner INS-1E cells were cultured in RPMI 1640 medium containing 11 mM glucose (Invitrogen, Switzerland) supplemented with 10 mM Hepes (pH 7.3), 10% (v/v) heat-inactivated fetal calf serum (Brunschwig AG, Switzerland), 50 μM β-mercaptoethanol, 1 mM sodium pyruvate, 50 μg/ml penicillin and 100 μg/ml streptomycin. Human TMEM27 cDNA (5183554, Invitrogen) was subcloned into pTRE2 vector (631008, Clontech), which was used for transfection and generation of INS-1 derived stable cell line following procedures described by Wang et al. The clone, INS-hTMEM27*F2, shows highest inducibility and lowest background is selected. As shown by Western blotting in FIG. 3, hTMEM27 protein could be induced dose-dependently by doxycycline.

FIG. 3: Cells were cultured for 24 h in the presence of indicated concentrations of doxycycline. Immunoblotting was performed with horseradish peroxidase-conjugated mouse anti-human TMEM27 monoclonal antibody (clone 3/3) followed by chemiluminescence detection.

Generation of Mouse Anti-TMEM27 Monoclonal Antibody Using Whole Cell Immunization Immunisation of swiss albino mice was performed with INS-h-TMEM27 clone F2 INS-1 cells, by repeated injection of living cells. As soon as the animals showed a specific immune-response to hTMEM27, the spleen cells were removed and fused to Ag8 cells according to G. Köhler and C. Milstein (1975) "Continuous cultures of fused cells secreting antibody of predefined specificity". Nature 256:495-497.

Incubation of TMEM27-8/9-Alexa488-IgG and TMEM27-8/9-Alexa555-Fab with living INS-hTMEM27 cells INS-h-TMEM27 clone F2 WT cells grown on PDL-coated glass-slides and incubated at 37° C.

Addition of the mAb's in different concentrations to inducing medium (complete cult.med+500 ng/ml-Doxycycline): 0.6 ml/well and incubation at 33° C. for 24 hrs. Cells are then washed 1× with Dulbeccos PBS(+$Ca^{2+}$/+$Mg^{2+}$) and fixed with 2% formaldehyde.

FIG. 4*a*-4*k* show the results of incubation of TMEM27-8/9-Alexa488-IgG and TMEM27-8/9-Alexa555-Fab with living INS-hTMEM27 cells.

TMEM27 is Located at Beta-Cells of Human and Monkey Pancreatic Islets

Formalin-fixed paraffin-embedded (FFPE) sections were used to assemble slides. Samples were dehydrated sequentially soaking the slides in xylol (×2), 100% EtOH, 95% EtOH, 80% EtOH, 70% EtOH, and 1×PBS (3 minutes each). Antigen retrieval was performed by soaking the slides in 1× citrate buffer and boiling them in a microwave (at 850 watts) for 3 minutes. After rinsing the slides twice with water, cells were permeabilized with 100 μL of 0.2% Triton in 1×PBS for 10 minutes at RT. After 3 washings with 1×PBS, blocking with 2% BSA in 1×PBS for 30' to 1 h at RT was done. Three more washings with 1×PBS preceded the Ab incubation (1-2 hours at 37° C. or O/N at 4° C.). Three more washings and DAPI staining (5-10 minutes at RT in the dark). Three final washings and assembling of the cover slips.

FIG. 5: Immunohistochemistry staining of FDA-approved human tissue microarrays. Paraffin sections of human tissue microarrays were stained with Alexa488-conjugated anti-TMEM27 (clone 8/9).

Anti-TEMEM27 stains specifically human and monkey beta-cells.

FIGS. 6*a*, 6*b* and 7: Immunohistochemistry staining of human and monkey pancreas. Paraffin sections of human and monkey pancreas were stained with Alexa488 conjugated TMEM27 (8/9).

Quantification of Cellular siRNA Uptake, Using TMEM27 Antibody as Vehicle.

siRNA Preparation.

Oligoribonucleotide Synthesis

Oligoribonucleotides were synthesized according to the phosphoramidite technology on solid phase employing an ABI 394 synthesizer (Applied Biosystems) at the 10 μmol scale. For RNA sequence information see table 1. Syntheses were performed on a solid support made of controlled pore glass (CPG, 520 Å, with a loading of 75 μmol/g, obtained from Prime Synthesis, Aston, Pa., USA). Regular RNA phosphoramidites, 2'-O-Methylphosphoramidites as well as ancillary reagents were purchased from Proligo (Hamburg, Germany). Specifically, the following amidites were used: (5'-O-dimethoxytrityl-N6-(benzoyl)-2'-O-t-butyldimethylsilyl-adenosine-3'-O-(2-cyanoethyl-N,N-diisopropylamino) phosphoramidite, 5'-O-dimethoxytrityl-N4-(acetyl)-2'-O-t-butyldimethylsilyl-cytidine-3'-O-(2-cyanoethyl-N,N-diisopropylamino) phosphoramidite, (5'-O-dimethoxytrityl-N2-(isobutyryl)-2'-O-t-butyldimethylsilyl-guanosine-3'-O-(2-cyanoethyl-N,N-diisopropylamino) phosphoramidite, and 5'-O-dimethoxytrityl-2'-O-t-butyldimethylsilyl-uridine-3'-O-(2-cyanoethyl-N,N-diisopropylamino) phosphoramidite. 2'-O-Methylphosphoramidites carried the same protecting groups as the regular RNA amidites with the exception of 2'-O-methyl-cytidine which was N4-(t-butylphenoxyacetyl) protected. All amidites were dissolved in anhydrous acetonitrile (100 mM) and molecular sieves (3 Å) were added. To generate the sulfhydryl linker at the 5'-end of the oligomer the 1-O-Dimethoxytrityl-hexyl-disulfide, 1'-[(2-cyanoethyl)-(N,N-diisopropyl)]-phosphoramidite linker from Glen Research (Sterling, Va., USA) was used. Prior to mAb conjugation the disulfide linker was reduced using TCEP (see below). For Cy5 conjugation the oligoribonucleotides was equipped with a C-6 aminolinker at its 5'-end using the 6-(4-Monomethoxytritylamino)hexyl-(2-cyanoethyl)-(N,N-diisopropyl)-phosphoramidite (Glen Research). 5-Ethyl thiotetrazole (ETT, 500 mM in acetonitrile) was used as activator solution. Coupling times were 6 minutes. In order to introduce phosphorothioate linkages a 100 mM solution of 3-ethoxy-1,2,4-dithiazoline-5-one (EDITH, obtained from Link Technologies, Lanarkshire, Scotland) in anhydrous acetonitrile was employed. The Cy5 fluorescent dye was attached to the 5'-end using the corresponding NHS ester (obtained from GE Healthcare, Munich, Germany) and the oligoribonucleotide carrying the C6 aminolinker.

Cleavage and Deprotection of Support Bound Oligomer

After finalization of the solid phase synthesis, the dried solid support was transferred to a 15 mL tube and treated with methylamine in methanol (2M, Aldrich) for 180 min at 45° C. After centrifugation the supernatant was transferred to a new 15 mL tube and the CPG was washed with 1200 μL N-methylpyrrolidin-2-one (NMP, Fluka, Buchs, Switzerland). The washing was combined with the methanolic methylamine solution and 450 μL Triethylamine trihydrofluoride (TEA.3HF, Alfa Aesar, Karlsruhe, Germany) was added. This mixture was brought to 65° C. for 150 min. After cooling to RT 0.75 mL NMP and 1.5 mL of ethoxytrimethylsilane (Fluka, Buchs, Switzerland) was added. 10 min later, the precipitated oligoribonucleotide was collected by centrifugation, the supernatant was discarded and the solid was reconstituted in 1 mL buffer A (see below).

Purification of Oligoribonucleotides

Crude oligoribonucleotides were purified by strong anion exchange (SAX) HPLC employing a preparative 22×250 mm DNA Pac 100 column (Dionex, Idstein, Germany) on an AKTA Explorer system (GE Healthcare). Buffer A consisted of 10 mM NaClO4, 1 mM EDTA, 10 mM Tris, pH 7.4, 6M Urea and 20% acetonitrile. Buffer B had 500 mM NaClO4 in Buffer A. A flow rate of 4.5 mL/min was employed. UV traces at 260 and 280 nm were recorded. A gradient of 20% B to 45% B within 55 min was employed. Appropriate fractions were pooled and precipitated with 3M NaOAc, pH=5.2 and 70% Ethanol.

Crude labeled oligomers were purified by RP HPLC using a XTerra Prep MS C8 10×50 mm column (Waters, Eschborn, Germany) on an AKTA Explorer system (GE Healthcare). Buffer A was 100 mM triethylammonium acetate (Biosolve, Valkenswaard, The Netherlands) and buffer B contained 50% acetonitrile in buffer A. A flow rate of 5 mL/min was employed. UV traces at 260, 280 and 643 nm (in case of Cy5) were recorded. A gradient of 5% B to 60% B within 58 column volumes (CV) was employed. Appropriate fractions were pooled and precipitated with 3M NaOAc, pH=5.2 and 70% Ethanol.

Finally, the purified oligomer was desalted by size exclusion chromatography on a column containing Sephadex G-25 (GE Healthcare). The concentration of the solution was determined by absorbance measurement at 260 nm in a UV photometer (Beckman Coulter, Krefeld, Germany). Until annealing the individual strands were stored as frozen solutions at −20° C.

Annealing of Oligoribonucleotides to Generate siRNA

Complementary strands were annealed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 95° C. which was cooled to RT within 3 h.

siRNA activation: The Cy5 labelled siRNA having a C6SSC6-Linker to a single de-oxythymidine was reduced with TCEP (Tris[2-carboxyethyl]phosphine) to selectively reduce the disulfide bonds.

The sulfhydryl-containing siRNA was then added to react with the maleimide groups already attached to the monoclonal antibody. Unreacted free sulfhydryls on siRNA were then blocked using NEM (N-Ethylmaleimide) and the final product purified by size exclusion using a 100 kD-cutoff concentration procedure.

The final labelling-ratio is determined with the nanodrop (IgG adsorption at 280 nm, Cy5 at 652 nm, Extinction coefficient Cy5: 250'000).

Sample Preparation

Day 1: Native INS-1E cells or INS-hTMEM27*F2 cells were seeded 50,000/well in a 96-well plate Day 3: Medium was replaced with culture medium containing 500 ng/ml doxycycline (Sigma-Aldrich) or culture medium for non-induced control samples.

Day 4: I-buffer was prepared and heated to 37° C. (1×HBSS, 20 mM Hepes, 0.1% BSA, prepared with tri-distilled water, pH 7.0). The solution of antibody either conjugated to siRNA-Cy5 (67 nM antibody, labelled with siRNA-Cy5 with average 2.4 molecules pr antibody for TMEM antibody, molecular ratio 2.2 for mGluR7 control antibody conjugate) or mixed with siRNA-Cy5 (67 nM antibody and 160 nM siRNA-Cy5) were prepared and equilibrated at 37° C. for 5 minutes. The cell-culture medium was gently aspirated, replaced with 60 µl/well of the antibody solution and incubated for 1 hour at 37° C. temperature.

For cell surface immunostaining, a 1:400 solution of Alexa647 goat-anti-mouse secondary antibody was prepared with icecold PBS. The wells were washed three times with 90 µl/well icecold PBS. The plate was transferred to an icebath, 60 µl/well of the icecold antibody solution was added to the wells and the plate was incubated for 60 minutes. The wells were washed three times with 90 µl/well PBS at room temperature. Then 100 µl/well of 4% formaldehyde were added, and the wells were incubated for 15 minutes at room temperature. The solution was replaced with 60 µl PBS/well containing 2 µg/ml CellMaskBlue and incubated for 20' at RT. The cells were washed once with 90 µl/well PBS at room temperature. A solution of 3 µM hoechst and 4% formaldehyde in PBS was added, and the wells were incubated for 15 minutes

TABLE 1 siRNA sequence information

| Seq. Id. No. | Sense strand sequence (5'- 3') | Seq. Id. No. | Antisense strand sequence (5'- 3') |
|---|---|---|---|
| Seq. Id. No. 1 | uuuGcAGAAAAGGuuGcAAdTsdT | Seq. Id. No. 4 | UUGcAACCUUUUCUcAAAdTsdT |
| Seq. Id. No. 2 | (C6SSC6)uuuGcAGAAAAGGuuGcAAdTsdT | Seq. Id. No. 5 | UUGcAACCUUUUCUGcAAAdTsdT |
| Seq. Id. No. 3 | (C6SSC6)uuuGcAGAAAAGGuuGcAAdTsdT | Seq. Id. No. 6 | (Cy5)(NHC6)UUGcAACCUUUUCUGcAAAdTsdT | lower case letters: 2'OMe nucleotide; s: phosphorothioate linkage; dT: deoxythymidine; (C6SSC6): C-6 disulfide linker; (NHC6): C-6 aminolinker; (Cy5): cyanine 5 dye Antibody—siRNA Conjugate Preparation Maleimide activation of the antibody: The monoclonal antibody TMEM27-8/9 was reacted with a 10-fold molar excess of the SMCC (sulfosuccinimidyl 4-[N maleimidomethyl]cyclohexane-1-carboxylate), followed by removal of excess (non re-acted) reagent by desalting.

at room temperature. The cells were washed once with PBS at room temperature and left in 150 µl PBS/well.

Quantification of Subcellular Level of Immunostain

Subcellular localization of antibody and siRNA-Cy5 was quantified using an Opera QEHS HCS reader from Evotec Technologies, Hamburg, Germany. This machine is equipped with an inverted confocal fluorescence microscope and is set up to do automated acquisition of images from samples prepared in clear bottom microtiter plates. In the reader, the software "Accapella" for image analysis is integrated, where image analysis methods (scripts) can be prepared, which identifies the localization of predefined types of objects.

The script that was used for the quantification in this example was developed to identify the intensity of immuno stain respectively on the cell surface region and localized in the intracellular cytoplasmic region. The analysis is based on three images acquired in parallel of samples stained with a DNA-specific fluorophore and the homogenous cell stain CellMaskBlue, secondary antibody labelled with Alexa488 and the siRNA label Cy5. From each image, objects are identified. From the first image specific for the DNA stain and CellMaskBlue stain, the number, position, size and shape of the nuclei was determined from the brighter hoechst stain, and the outline of the cytoplasm from the CellMaskBlue stain. From the second image selective for Alexa488 secondary antibody, the areas with cell surface immunostaining was determined and the intensity quantified. From the third, the intensity of Cy5 staining in the cytoplasmic region of the cells was identified and the fluorescence intensity quantified.

Figure 8:
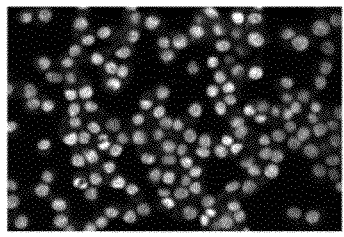
Figure 8:
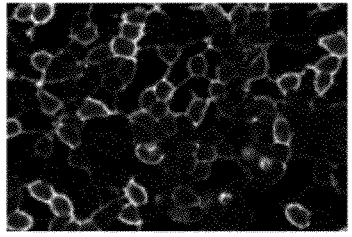
Figure 8:
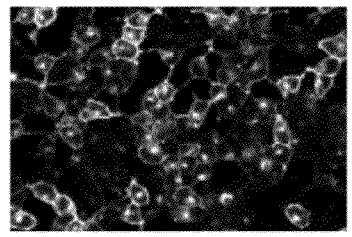
Figure 8:
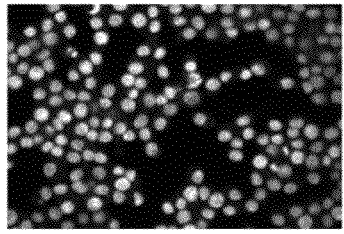
Figure 8:
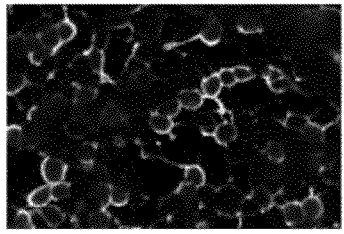
Figure 8:
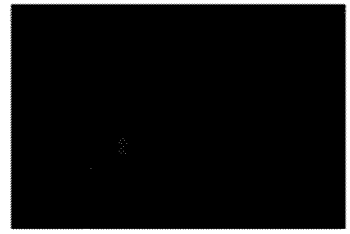
Figure 8:
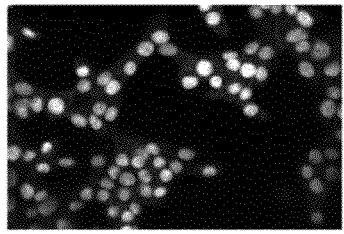
Figure 8:
Figure 8:
Figure 8:
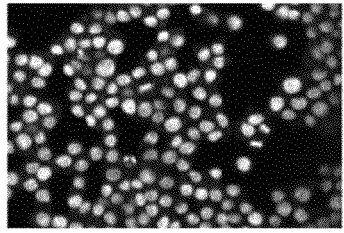
Figure 8:
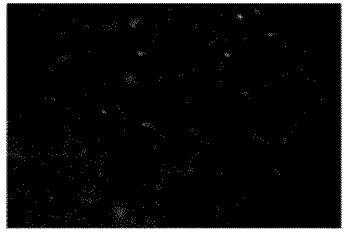
Figure 8:
Figure 9A:
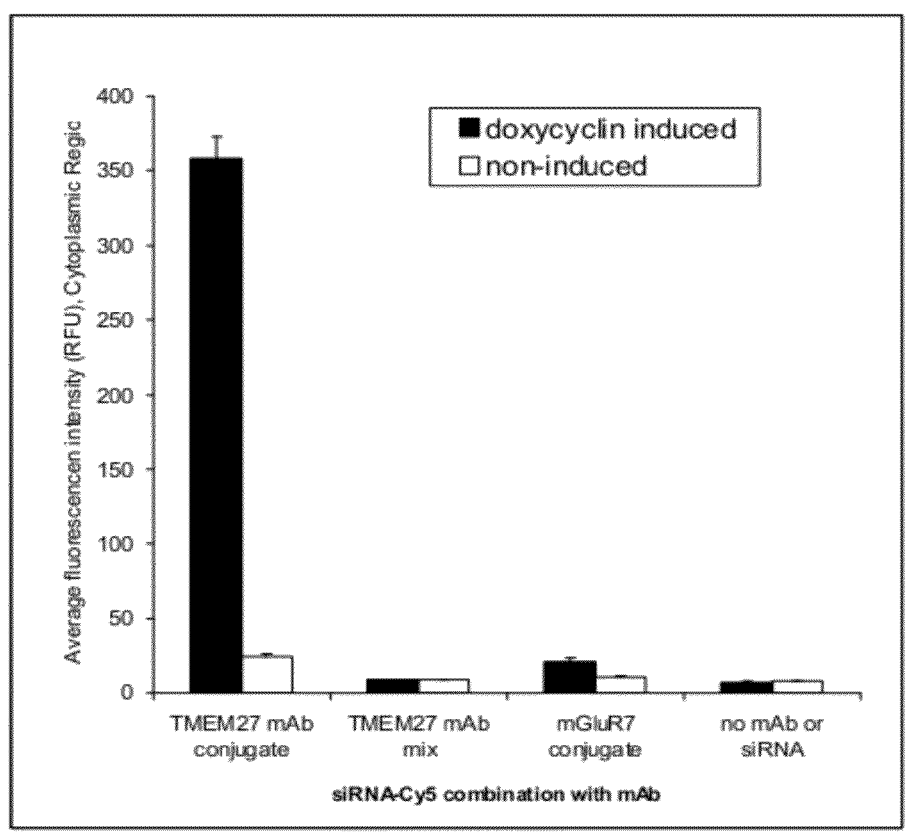
Figure 9B:
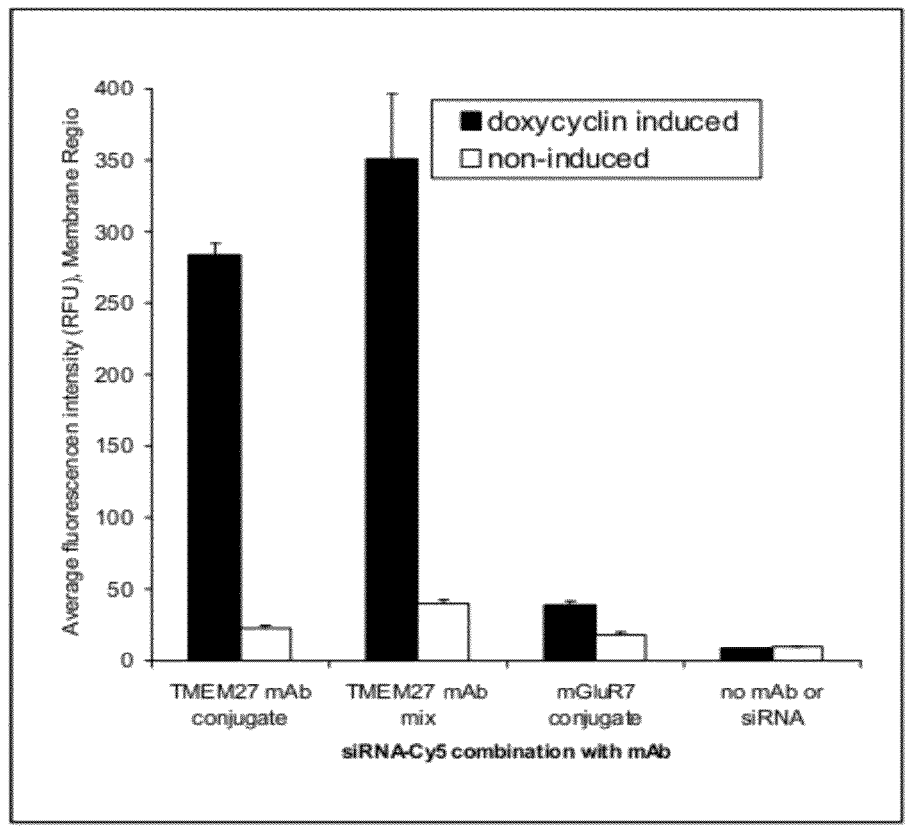

FIG. 8 shows images of INS-hTMEM27*F2 cells which have been incubated with 67 nM primary antibody conjugated with siRNA-Cy5 or a mix of 67 nM primary antibody and 160 nM siRNA-Cy5 at 37° C. before washed and transferred to ice for secondary staining and fixation as described in the protocol. Each row contains images acquired in parallel of the same field of view in the well. Panel A-F are cells induced with doxycyclin. Panel G-I are images of samples prepared as the samples in panel A-C except using non induced cells. Panel J-L are images of samples prepared as the samples in panel A-C except the TMEM27 antibody siRNA-Cy5 conjugate was replaced with siRNA-Cy5 conjugated to an antibody recognizing the mGluR7 receptor.

Panel A, D, G and J show images acquired with filter settings selective for CellMaskBlue and hoechst stain: Laser 405 nm, emission reflected by Longpath 650 filter, filtered through Shortpath 568 filter and Bandpath 455/70 filter. Panel B, E, H and K show images acquired with filter settings selective for the cell surface stain with Alexa488 secondary antibody: Laser 488 nm, emission reflected by LP650 and LP568, filtered through BP535/60. Panel C, F and I show images acquired with filter settings selective for the siRNA label Cy5: Laser 635 nm, emission passing through LP650 and filtered through BP690/50. Intensity scaling in image is similar for images acquired with same camera.

The images demonstrate that TMEM27 antibody can mediate cellular uptake of siRNA through recognition of membrane imbedded human TMEM27.

FIG. 9 shows the quantified cell surface secondary antibody immunostaining and cytoplasmic region intensity of Cy5. The samples were prepared with doxycyclin induced human TMEM27 expressing (black bars) and non-induced (white bars) cells and incubated for 1 hour with different combinations of siRNA and antibody. From left to right on the x-axis: 67 nM TMEM27 8/9 primary antibody conjugated with siRNA-Cy5 (average 2.4 molecules pr antibody), a mix of 67 nM TMEM27 8/9 primary antibody and 160 nM siRNA-Cy5, 67 nM mGluR7 primary antibody conjugated with siRNA-Cy5 (average 2.2 molecules pr antibody) and finally samples incubated with buffer without siRNA or antibody at 37° C. for 1 hour before washed and transferred to ice for secondary staining and fixation as described in the protocol.

Panel 9a: Average pixel intensity of secondary antibody immunostain in cell surface membrane region. Panel 9b: Average Pixel intensity in Cytoplasmic Region of Cy5.

While there are shown and described presently preferred embodiments of the invention, it is to be distinctly understood that the invention is not limited thereto but may be otherwise variously embodied and practiced within the scope of the following claims.

The invention claimed is:

1. An antibody or antigen-binding portion thereof directed to human TMEM27, wherein the antibody comprises CDR1 to CDR3 of a $V_H$ domain of an antibody obtainable from hybridoma cell line TMEM27-8/9 (DSM ACC2995) and CDR1 to CDR3 of a $V_L$ domain of an antibody obtainable from hybridoma cell line TMEM27-8/9 (DSM ACC2995).

2. The antibody of claim 1, wherein the antibody comprises a $V_H$ domain and a $V_L$ domain of an antibody obtainable from hybridoma cell line TMEM27-8/9 (DSM ACC2995).

3. The antibody of claim 2, wherein the antibody is produced by hybridoma cell line TMEM27-8/9 (DSM ACC2995).

4. A composition comprising the antibody of claim 1 and a pharmaceutically acceptable carrier.

5. A conjugate comprising an antibody of claim 1 and an active compound covalently linked to the antibody.

6. The conjugate of claim 5, wherein the active compound is a toxin or a siRNA molecule.

7. The antibody of claim 1, wherein the antibody is a monoclonal, chimeric or humanized antibody.

8. A conjugate comprising an antibody of claim 1 and a positron-emitting radionuclide.

9. The conjugate of claim 8, wherein the positron-emitting radionuclide is selected from the group consisting of gallium-68 ($^{68}$Ga), fluorine-18 ($^{18}$F), copper-64 ($^{64}$Cu), yttrium-86 ($^{86}$Y) bromine-76 ($^{76}$Br), zirconium-89 ($^{89}$Zr), and iodine-124 ($^{124}$I).

10. A hybridoma cell line TMEM27-8/9 having the deposit number DSM ACC2995.

* * * * *

SEQUENCE LISTING

```
<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(3)
<223> OTHER INFORMATION: 2' O-Methyl nucleotide
<220> FEATURE:
<221> NAME/KEY: misc_feature
<222> LOCATION: (5)..(5)
<223> OTHER INFORMATION: 2' O-Methyl nucleotide
<220> FEATURE:
<221> NAME/KEY: misc_feature
<222> LOCATION: (14)..(15)
<223> OTHER INFORMATION: 2' O-Methyl nucleotide
<220> FEATURE:
<221> NAME/KEY: misc_feature
<222> LOCATION: (17)..(17)
<223> OTHER INFORMATION: 2' O-Methyl nucleotide
<220> FEATURE:
<221> NAME/KEY: misc_feature
<222> LOCATION: (20)..(20)
<223> OTHER INFORMATION: Deoxythymidine
<220> FEATURE:
<221> NAME/KEY: misc_feature
```

```
<222> LOCATION: (21)..(21)
<223> OTHER INFORMATION: s: phosphorothioate linkage
<220> FEATURE:
<221> NAME/KEY: misc_feature
<222> LOCATION: (22)..(22)
<223> OTHER INFORMATION: Deoxythymidine

<400> SEQUENCE: 1
uuugcagaaa agguugcaat st                                             22

<210> SEQ ID NO 2
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(3)
<223> OTHER INFORMATION: 2' O-Methyl nucleotide
<220> FEATURE:
<221> NAME/KEY: misc_feature
<222> LOCATION: (5)..(5)
<223> OTHER INFORMATION: 2' O-Methyl nucleotide
<220> FEATURE:
<221> NAME/KEY: misc_feature
<222> LOCATION: (14)..(15)
<223> OTHER INFORMATION: 2' O-Methyl nucleotide
<220> FEATURE:
<221> NAME/KEY: misc_feature
<222> LOCATION: (17)..(17)
<223> OTHER INFORMATION: 2' O-Methyl nucleotide
<220> FEATURE:
<221> NAME/KEY: misc_feature
<222> LOCATION: (20)..(20)
<223> OTHER INFORMATION: Deoxythymidine
<220> FEATURE:
<221> NAME/KEY: misc_feature
<222> LOCATION: (21)..(21)
<223> OTHER INFORMATION: s = phosphorothioate linkage
<220> FEATURE:
<221> NAME/KEY: misc_feature
<222> LOCATION: (22)..(22)
<223> OTHER INFORMATION: Deoxythymidine

<400> SEQUENCE: 2
uuugcagaaa agguugcaat st                                             22

<210> SEQ ID NO 3
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(3)
<223> OTHER INFORMATION: 2' O-Methyl nucleotide
<220> FEATURE:
<221> NAME/KEY: misc_feature
<222> LOCATION: (5)..(5)
<223> OTHER INFORMATION: 2' O-Methyl nucleotide
<220> FEATURE:
<221> NAME/KEY: misc_feature
<222> LOCATION: (14)..(15)
<223> OTHER INFORMATION: 2' O-Methyl nucleotide
<220> FEATURE:
<221> NAME/KEY: misc_feature
<222> LOCATION: (17)..(17)
<223> OTHER INFORMATION: 2' O-Methyl nucleotide
<220> FEATURE:
<221> NAME/KEY: misc_feature
<222> LOCATION: (17)..(17)
<223> OTHER INFORMATION: 2' O-Methyl nucleotide
<220> FEATURE:
<221> NAME/KEY: misc_feature
```

```
<222> LOCATION: (20)..(20)
<223> OTHER INFORMATION: Deoxythymidine
<220> FEATURE:
<221> NAME/KEY: misc_feature
<222> LOCATION: (21)..(21)
<223> OTHER INFORMATION: s = phosphorothioate linkage
<220> FEATURE:
<221> NAME/KEY: misc_feature
<222> LOCATION: (22)..(22)
<223> OTHER INFORMATION: Deoxythymidine

<400> SEQUENCE: 3
uuugcagaaa agguugcaat st                                          22

<210> SEQ ID NO 4
<211> LENGTH: 21
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (4)..(4)
<223> OTHER INFORMATION: 2' O-Methyl nucleotide
<220> FEATURE:
<221> NAME/KEY: misc_feature
<222> LOCATION: (15)..(15)
<223> OTHER INFORMATION: 2' O-Methyl nucleotide
<220> FEATURE:
<221> NAME/KEY: misc_feature
<222> LOCATION: (19)..(19)
<223> OTHER INFORMATION: Deoxythymidine
<220> FEATURE:
<221> NAME/KEY: misc_feature
<222> LOCATION: (20)..(20)
<223> OTHER INFORMATION: s = phosphorothioate linkage
<220> FEATURE:
<221> NAME/KEY: misc_feature
<222> LOCATION: (21)..(21)
<223> OTHER INFORMATION: Deoxythymidine

<400> SEQUENCE: 4
uugcaaccuu uucucaaats t                                           21

<210> SEQ ID NO 5
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (4)..(4)
<223> OTHER INFORMATION: 2' O-Methyl nucleotide
<220> FEATURE:
<221> NAME/KEY: misc_feature
<222> LOCATION: (16)..(16)
<223> OTHER INFORMATION: 2' O-Methyl nucleotide
<220> FEATURE:
<221> NAME/KEY: misc_feature
<222> LOCATION: (20)..(20)
<223> OTHER INFORMATION: Deoxythymidine
<220> FEATURE:
<221> NAME/KEY: misc_feature
<222> LOCATION: (21)..(21)
<223> OTHER INFORMATION: s = phosphorothoate linkage
<220> FEATURE:
<221> NAME/KEY: misc_feature
<222> LOCATION: (22)..(22)
<223> OTHER INFORMATION: Deoxythymidine

<400> SEQUENCE: 5
uugcaaccuu uucugcaaat st                                          22
```

-continued

```
<210> SEQ ID NO 6
<211> LENGTH: 22
<212> TYPE: DNA
<213> ORGANISM: Artificial Sequence
<220> FEATURE:
<223> OTHER INFORMATION: siRNA
<220> FEATURE:
<221> NAME/KEY: misc_feature
<222> LOCATION: (4)..(4)
<223> OTHER INFORMATION: 2' O-Methyl nucleotide
<220> FEATURE:
<221> NAME/KEY: misc_feature
<222> LOCATION: (16)..(16)
<223> OTHER INFORMATION: 2' O-Methyl nucleotide
<220> FEATURE:
<221> NAME/KEY: misc_feature
<222> LOCATION: (20)..(20)
<223> OTHER INFORMATION: Deoxythymidine
<220> FEATURE:
<221> NAME/KEY: misc_feature
<222> LOCATION: (21)..(21)
<223> OTHER INFORMATION: s = phosphorothioate linkage
<220> FEATURE:
<221> NAME/KEY: misc_feature
<222> LOCATION: (22)..(22)
<223> OTHER INFORMATION: Deoxythymidine

<400> SEQUENCE: 6
uugcaaccuu uucugcaaat st                                              22

<210> SEQ ID NO 7
<211> LENGTH: 222
<212> TYPE: PRT
<213> ORGANISM: Homo sapiens

<400> SEQUENCE: 7

Met Leu Trp Leu Leu Phe Phe Leu Val Thr Ala Ile His Ala Glu Leu
  1               5                  10                  15

Cys Gln Pro Gly Ala Glu Asn Ala Phe Lys Val Arg Leu Ser Ile Arg
             20                  25                  30

Thr Ala Leu Gly Asp Lys Ala Tyr Ala Trp Asp Thr Asn Glu Glu Tyr
         35                  40                  45

Leu Phe Lys Ala Met Val Ala Phe Ser Met Arg Lys Val Pro Asn Arg
     50                  55                  60

Glu Ala Thr Glu Ile Ser His Val Leu Leu Cys Asn Val Thr Gln Arg
 65                  70                  75                  80

Val Ser Phe Trp Phe Val Val Thr Asp Pro Ser Lys Asn His Thr Leu
                 85                  90                  95

Pro Ala Val Glu Val Gln Ser Ala Ile Arg Met Asn Lys Asn Arg Ile
            100                 105                 110

Asn Asn Ala Phe Phe Leu Asn Asp Gln Thr Leu Glu Phe Leu Lys Ile
        115                 120                 125

Pro Ser Thr Leu Ala Pro Pro Met Asp Pro Ser Val Pro Ile Trp Ile
    130                 135                 140

Ile Ile Phe Gly Val Ile Phe Cys Ile Ile Ile Val Ala Ile Ala Leu
145                 150                 155                 160

Leu Ile Leu Ser Gly Ile Trp Gln Arg Arg Arg Lys Asn Lys Glu Pro
                165                 170                 175

Ser Glu Val Asp Asp Ala Glu Asp Lys Cys Glu Asn Met Ile Thr Ile
            180                 185                 190
```

```
Glu Asn Gly Ile Pro Ser Asp Pro Leu Asp Met Lys Gly Gly His Ile
        195             200             205

Asn Asp Ala Phe Met Thr Glu Asp Glu Arg Leu Thr Pro Leu
    210             215             220
```